US011517266B2

(12) United States Patent
Batzer

(10) Patent No.: US 11,517,266 B2
(45) Date of Patent: Dec. 6, 2022

(54) DETECTION OF INTERFERENCE WHEN MEASURING BIOELECTRIC SIGNALS

(71) Applicant: Siemens Healthcare GmbH, Erlangen (DE)

(72) Inventor: Ulrich Batzer, Spardorf (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 337 days.

(21) Appl. No.: 16/816,742

(22) Filed: Mar. 12, 2020

(65) Prior Publication Data

US 2020/0297282 A1 Sep. 24, 2020

(30) Foreign Application Priority Data

Mar. 18, 2019 (DE) ........................ 102019203627.9

(51) Int. Cl.

| | |
|---|---|
| ***A61B 5/00*** | (2006.01) |
| ***G01R 19/25*** | (2006.01) |
| ***G01R 31/00*** | (2006.01) |
| ***A61B 5/318*** | (2021.01) |
| ***A61B 5/369*** | (2021.01) |
| ***A61B 5/389*** | (2021.01) |

(52) U.S. Cl.

CPC ............ *A61B 5/7203* (2013.01); *A61B 5/318* (2021.01); *A61B 5/369* (2021.01); *A61B 5/389* (2021.01); *G01R 19/2503* (2013.01); *G01R 31/001* (2013.01); *A61B 2562/182* (2013.01)

(58) Field of Classification Search

CPC ....... A61B 5/7203; A61B 5/318; A61B 5/369; A61B 5/389; A61B 2562/182; A61B 5/7225; A61B 5/72; A61B 5/7221; G01R 19/2503; G01R 31/001; G01R 19/0084; G01R 19/10; G01R 31/54; G01R 19/0023; H05K 9/002

USPC ......................................... 324/627, 612, 600

See application file for complete search history.

(56) References Cited

U.S. PATENT DOCUMENTS

| | | | | |
|---|---|---|---|---|
| 10,110,239 | B1 * | 10/2018 | Shu | H03K 5/1565 |
| 10,869,600 | B2 * | 12/2020 | Cho | A61B 5/0006 |
| 10,912,418 | B2 * | 2/2021 | Zernhelt | A47J 42/40 |
| 2016/0095528 | A1 | 4/2016 | Batzer et al. | |
| 2016/0131699 | A1 * | 5/2016 | Hamilton | G01R 1/07 324/750.01 |

(Continued)

FOREIGN PATENT DOCUMENTS

| | | | |
|---|---|---|---|
| DE | 2162040 | A1 | 6/1973 |
| DE | 102015204207 | A1 | 9/2016 |
| DE | 102015219037 | A1 | 4/2017 |

OTHER PUBLICATIONS

German Office Action for German Application No. 102019203627.9 dated Dec. 12, 2019.

*Primary Examiner* — Giovanni Astacio-Oquendo

(74) *Attorney, Agent, or Firm* — Harness, Dickey & Pierce, P.L.C.

(57) ABSTRACT

A detection apparatus is for detecting interference on signal paths in a differential voltage measuring system with a signal measuring circuit for measuring bioelectric signals with a number of useful signal paths having at least one shield. In an embodiment, the detection apparatus includes at least one analysis unit, connected to the shield and embodied to detect interference in a useful signal path of the voltage measuring system via a signal measured at the shield in the case of interference.

24 Claims, 4 Drawing Sheets

(56) References Cited

U.S. PATENT DOCUMENTS

| | | | |
|---|---|---|---|
| 2016/0228024 | A1 | 8/2016 | Batzer et al. |
| 2016/0262644 | A1 | 9/2016 | Batzer |
| 2017/0099528 | A1 | 4/2017 | Batzer |
| 2019/0353692 | A1 | 11/2019 | Batzer |
| 2021/0186401 | A1* | 6/2021 | Batzer ...................... A61B 5/25 |
| 2022/0054021 | A1* | 2/2022 | Batzer .................. A61B 5/7289 |

* cited by examiner 1
27
14
16
16'
15
BS, BS*
PS
40
25a
25b
25c
25d
K
6a
6b
7N
S
UEKG34
4
5
3
P
E
UEKG45
UEKG35
UCM
nsource(t)

DETECTION OF INTERFERENCE WHEN MEASURING BIOELECTRIC SIGNALS

PRIORITY STATEMENT

The present application hereby claims priority under 35 U.S.C. § 119 to German patent application number DE 102019203627.9 filed Mar. 18, 2019, the entire contents of which are hereby incorporated herein by reference.

FIELD

Embodiments of the invention generally relate to a detection apparatus and a method for detecting interference in a differential voltage measuring system with a signal measuring circuit for measuring bioelectric signals with a number of useful signal paths. Embodiments of the invention moreover generally relate to a voltage measuring system with such a detection apparatus.

BACKGROUND

Voltage measuring systems, in particular differential voltage measuring systems, for measuring bioelectric signals are, for example, used in medicine for measuring electrocardiograms (ECGs), electroencephalograms (EEGs) or electromyograms (EMGs). With such applications, preferably a high input impedance of at least several MOhm should be observed on every measuring channel in order to reduce, or at least not amplify, the influence of interference. The high input impedance desired should also be maintained in the cables of the above-mentioned devices for measuring bioelectric signals. The measuring leads of the cables are usually surrounded by a shield. To obtain better handleability, the cables are moreover flexible, narrow and light. However, these features lead to a conflict between the lifetime and the handleability of the cables and increase the risk of a cable defect.

The causes of defective cables K are, for example, broken leads or often kinks D (see FIG. 5). Kinks can occur after torsion or bending of the long cables K when the measuring leads bulge and do not return to their in original shape. The bulging measuring leads can then rupture the lead insulation and contact the shield S and this can lead to reduced input impedance in the cables K and hence to amplification of interference. Herein, the problem is that, without a special test environment, such interference cannot always be unequivocally attributed to reduced input impedance in the cables K. Moreover, kinks D and other input impedance-reducing cable defects often occur in the form of loose connections and this also hinders fault detection. Therefore, there is a risk of a defective cable being used unintentionally until the signal quality is no longer sufficient to enable bioelectric measurements and examinations to be carried out.

A common solution for avoiding or detecting interference due to reduced input impedance in the cables is to replace the cables at regular intervals or at least have them examined by service personnel. When the cables are checked by service personnel, a reference signal generated by a simulator is output to the cable to be examined. The cable is then moved and an output signal is measured. This output signal is compared with the reference signal and checked as to whether there are differences between the two signals and hence interference. However, the degree of interference with which a cable break is assumed is based on expert opinion. Moreover, such checking is relatively laborious.

SUMMARY

The inventors have discovered that a further type of interference that can occur when measuring bioelectric signals is interference signals coupled-in or present on the patient or in the cables. Such interference signals comprise, for example, ambient electromagnetic fields, electrostatic charges and the like.

The inventors therefore aim to reduce or even avoid interference when measuring bioelectric signals in at least one embodiment.

Embodiments are directed to a detection apparatus as, a voltage measuring system and a method.

In at least one embodiment, a detection apparatus is used to detect interference on signal paths in a differential voltage measuring system with a signal measuring circuit for measuring bioelectric signals with a number of useful signal paths having a shield. In at least one embodiment, the detection apparatus comprises at least one analysis unit. The latter is connected to the shield and embodied to detect interference in a useful signal path of the voltage measuring system by way of a signal measured at the shield in the case of interference.

In at least one embodiment, a detection apparatus is for detecting interference on signal paths in a differential voltage measuring system including a signal measuring circuit for measuring bioelectric signals with a number of useful signal paths including at least one shield, the detection apparatus comprising:

at least one analysis unit, connected to the shield and embodied to detect interference in a signal path of the voltage measuring system via a signal measured at the shield.

In at least one embodiment, a voltage measuring system comprises:

at least one signal measuring circuit including a number of signal paths for measuring bioelectric signals; and the detection apparatus of an embodiment.

In at least one embodiment, a method is for detecting interference on signal paths in a differential voltage measuring system including a signal measuring circuit for measuring bioelectric signals with a number of signal paths and including a shield, the method comprising:

measuring signals at the shield; and detecting interference based upon an analysis of the signals measured.

In at least one embodiment, a non-transitory computer program product stores a computer program, directly loadable into a storage facility of a voltage measuring system, including program segments for executing the method of an embodiment when the computer program is executed in the voltage measuring system.

In at least one embodiment, a non-transitory computer-readable medium stores program segments, readable-in and executable by a computing unit, to perform the method of an embodiment when the program segments are executed by the computing unit.

BRIEF DESCRIPTION OF THE DRAWINGS

The following describes the invention again in more detail with reference to the attached figures and example embodiments. Herein, the same components are provided with identical reference characters in the different figures.

As a rule, the figures are not true to scale. The figures show.

DETAILED DESCRIPTION OF THE EXAMPLE EMBODIMENTS

Figure 1:
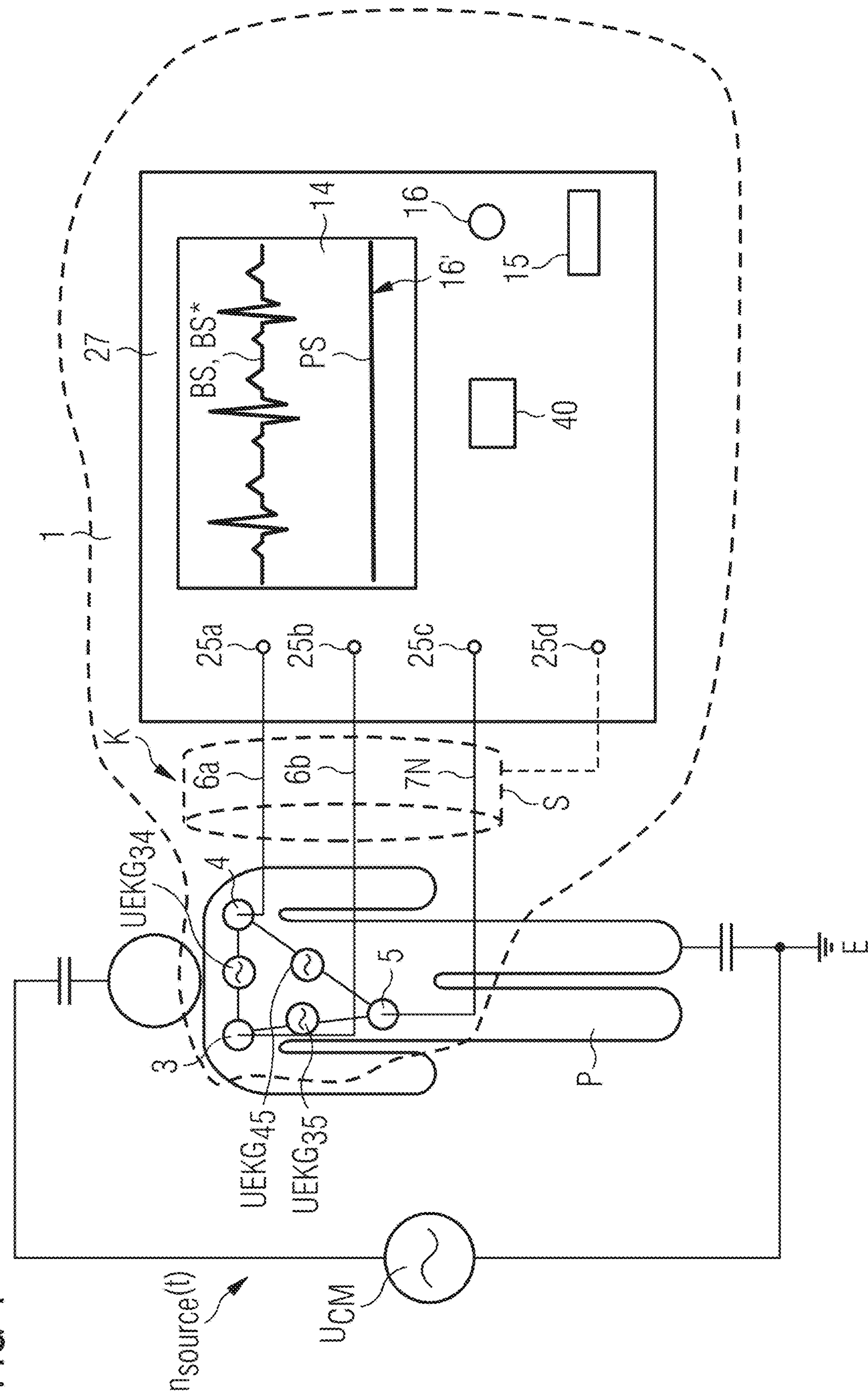
FIG. 1 schematically shows an example embodiment of a differential voltage measuring system including possible positioning of the electrical connectors or contacts of an on a patient, FIG. 2 schematically shows a differential voltage measuring system with a detection apparatus according to an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In at least one embodiment, a detection apparatus is used to detect interference on signal paths in a differential voltage measuring system with a signal measuring circuit for measuring bioelectric signals with a number of useful signal paths having a shield. In at least one embodiment, the detection apparatus comprises at least one analysis unit. The latter is connected to the shield and embodied to detect interference in a useful signal path of the voltage measuring system by way of a signal measured at the shield in the case of interference.

As already mentioned in the introduction, the differential voltage measuring system detects bioelectric signals, for example from a human or animal patient. For this purpose, it has a number of measuring leads or useful signal paths. These connect, for example as individual cables, electrodes attached to the patient to detect the signals with the further components of the voltage measuring system, i.e. in particular the electronics that are used to evaluate or display the detected signals.

The basic mode of operation of differential voltage measuring systems is known to the person skilled in the art and therefore no more detailed explanation will be given here. They can in particular be embodied as electrocardiograms (ECGs), electroencephalograms (EEGs) or electromyograms (EMGs).

The useful signal paths have at least one shield. The shield is used to keep electrical and/or magnetic fields in particular occurring at higher frequencies remote from the useful signal paths. Herein, it operates in accordance with the principle of induction or as a Faraday cage and is, for example, embodied as a metallic foil surrounding the conductor of the useful signal path, but insulated therefrom. Herein, every useful signal path can have a separate shield in the sense that each shield is attached to its own reference potential or its own evaluation electronics. However, the useful signal paths preferably have a common shield in the sense that shield parts surrounding individual useful signal paths are connected in an electrically conductive manner and attached to a common reference potential or common electronics.

Herein, the shield can in principle be embodied as passive in that it is connected to the frame potential of the signal measuring circuit. However, it can preferably also be actuated actively via a corresponding driver in order to compensate the influences of any interference fields.

Herein, interference describes both interference signals, for example couplings into the cables or via a patient, and signal path defects such as, for example, cable breaks, kinks or the like. Couplings-in occur when measuring bioelectric signals, for example ECG signals, for example frequently called common-mode interference signals or common-mode signals (CM signals).

The analysis unit is embodied to detect interference in a useful signal path of the voltage measuring system. Therefore, according to at least one embodiment of the invention, interference is detected in that—in optimal cases, unexpected—signal, i.e. for example a bioelectric signal and/or a CM signal on the shield is measured and optionally analyzed in greater detail.

Herein, the analysis unit can in principle have different embodiments. The detection apparatus can comprise exactly one, or, in other embodiments, more analysis units, such as, for example, a defect analysis unit and an interference signal evaluation unit. The analysis unit can preferably have an integrated circuit, particularly preferably an ASIC. However, the analysis unit can also preferably comprise a microcontroller or another universal computing unit.

With the method for detecting interference on signal paths in the previously explained voltage measuring system, signals are measured at the shield. Interference is then detected based on an analysis of the measured signals. This analysis is performed via the analysis unit.

The voltage measuring system has at least one signal measuring circuit with a number of useful signal paths for measuring bioelectric signals and a detection apparatus according to at least one embodiment of the invention.

In contrast to the prior art in which only the useful signal paths or the actual cables to be checked are themselves checked, therefore, according to at least one embodiment of the invention, measurements and checks are performed on the shield as to whether the useful signal paths are defective or other types of interference have cross-coupled onto the shield. In contrast to applications known from practice, this does not require the useful signal paths to be connected to the patient. Therefore, the method according to at least one embodiment of the invention enables tests to be performed at any time, for example ahead of an examination or also during the examination, to determine whether all the cables are in proper service condition and/or whether strong electromagnetic fields are coupled into the cables.

A further advantage of the apparatuses and methods according to embodiments of the invention described here is that a technician or service engineer is no longer required in order to detect a cable defect. The measurement on the shield can proceed in parallel and automatically during a useful signal measurement and a cable defect can be rendered immediately visible, for example on a user interface of the voltage measuring system. Therefore, the signal path defect, or cable defect, can be discovered immediately, for example by the actual operator, and the cable can be replaced immediately and a correct measurement can be carried out. Therefore, this also reduces the risk of measurements continuing to be taken with cables with undetected damage.

Moreover, the type of useful signal is of no importance when detecting interference via the shield. Therefore, the detection apparatus according to at least one embodiment of the invention can be used for a wide variety of voltage measuring systems, such as, for example, ECG measuring systems, EEG measuring systems or EMG measuring systems without having to be specifically adapted for the purpose. This also enables enormous savings on development and manufacturing costs.

Furthermore, the detection apparatus does not require an external voltage source for the detection of interference since all relevant current-carrying parts can be integrated, or are integrated, in the detection apparatus or the voltage measuring facility. This enables a completely passive test structure.

A detection apparatus, in particular according to at least one embodiment of the invention, for detecting interference on signal paths in a differential voltage measuring system with a signal measuring circuit for measuring bioelectric signals with a number of useful signal paths has an interference signal evaluation unit. This in turn comprises an interference signal determining unit, which is embodied to determine an interference signal with a frequency in the range of a mains frequency. The interference signal evaluation unit furthermore comprises an interference signal suppressing unit, which is embodied to reduce interference signal components in the bioelectric signals based on the interference signal determined.

The detection apparatus described here can also be used as an independent concept independently of the above-described detection apparatus, i.e. also without using the shield for detecting interference, when the interference signals are detected in another way, for example on a separate interference signal path. However, special synergetic effects are obtained when the determination of the interference signal according to at least one embodiment of the invention in the range of the mains frequency takes place by a measurement at the shield. This is because the shield represents an electrical conductor with the same length as the useful signal paths. Ambient electromagnetic fields, which are generally dominated by the common-mode component of the mains frequency, are therefore coupled into the shield similarly to the coupling into the useful signal path. Therefore, in particular these components should be advantageously be measured for the further analysis of the actual interference signals and the influence thereof on the bioelectric signals that are actually to be measured at the shield.

The mode of operation of a differential voltage measuring system has been described in detail above. The mains frequency designates the frequency of the mains voltage usually provided throughout the country by power supply companies or at least the frequency of the voltage of the electric circuit to which the detection apparatus is attached. It has been found that the determination of interference signals can be greatly simplified if the frequency range of the interference signals is limited.

Therefore, according to at least one embodiment of the invention, the interference signal determining unit only determines interference signals, in particular CM signals, within the range of the mains frequency. Since these usually represent the largest interference signal components, this results in a significant simplification of the signal analysis. During the signal analysis, the strongest signal in the frequency range around the mains frequency is sought, for example by way of a frequency analysis. This then has a high probability of representing the mains interference since, as a rule, no useful signal components are found on the interference signal paths.

The signal found is then subsequently used for interference signal suppression, as will be explained in more detail later. However, herein, the signal is not, as was formerly usual, deformed in a wide range, which would reduce the diagnostic value, but rather only changed precisely within the usual tolerances at the previously determined frequency of the interference signal such that the influences of the interference signal are reduced or compensated.

The type of useful signal is of no importance when detecting interference via the shield and/or based on a range around the mains frequency. Therefore, the detection apparatus according to the invention can be used for a wide variety of voltage measuring systems, such as, for example, ECG measuring systems, EEG measuring systems or EMG measuring systems without having to be specifically adapted for the purpose. This also enables enormous savings on development and manufacturing costs.

Furthermore, the detection apparatus does not require an external voltage source for the detection of interference since all relevant current-carrying parts can be integrated, or are integrated, in the detection apparatus or the voltage measuring facility. This enables a completely passive test structure.

Herein, the detection apparatus can in each case be an independent component and, for example, be installed, connected upstream or interconnected as a retrofit kit in existing ECGs, EEGs or EMGs, for example via plug-in connectors, as will be explained in more detail later. However, the detection apparatus is preferably already permanently integrated in a voltage measuring system according to at least one embodiment of the invention.

A large proportion of the above-mentioned components of the detection apparatus, in particular the analysis unit, can be wholly or partially implemented in the form of software modules in a processor of a corresponding voltage measuring system. An extensively software-based implementation has the advantage that it is also possible to retrofit voltage measuring systems used to date in a simple way via a software update in order to work in the manner according to the invention. In this regard, the object is also achieved by a corresponding computer program product with a computer program, which can be loaded directly into storage facility of a voltage measuring system, with program segments for executing all the steps of the method according to the invention method when the program is executed in the voltage measuring system. In addition to the computer program, such a computer program product can optionally comprise additional parts such as, for example, documentation and/or additional components and also hardware components, such as, for example, hardware keys (dongles etc.) for using the software.

Transportation to the voltage measuring system and/or storage on or in the voltage measuring system can take place via a computer-readable medium, for example a memory stick, a hard disk or another transportable or permanently installed data carrier on which the program segments of the computer program which can be read-in and executed by a computing unit of the voltage measuring system are stored. To this end, the computing unit can, for example, have one or more interacting microprocessors or the like.

Further, particularly advantageous and developments of the invention can be derived from the claims and the following description, wherein the claims of one claim category can also be developed analogously to the claims and descriptive parts of another claim category and in particular individual features of different example embodiments or variants can be combined to form new example embodiments or variants.

The detection apparatus according to at least one embodiment of the invention preferably comprises at least one current application unit, which is embodied to impress a signal on a first useful signal path. The detection apparatus according to the invention furthermore preferably comprises a defect analysis unit as an analysis unit, which detects a signal path defect in a useful signal path of the voltage measuring system by way of the previously impressed signal measured at the shield in the case of interference.

Herein, the current application unit is preferably embodied such that it preferably impresses an arbitrary but defined first signal on a first useful signal path of the signal measuring circuit of the voltage measuring system. The signal can preferably be a current, which can be directly or indirectly impressed and measured. For example, the current can preferably be impressed on a useful signal path via a current source. However, the current can also particularly preferably be impressed or regulated indirectly on the useful signal path via a pull-up resistor and/or a pull-up-down resistor. Herein, the impressed current is preferably in the nanoampere range in order, for example, not to falsify measured bioelectric signals and in this way to exclude the possibility of a patient being endangered.

If the useful signal path is, for example, connected to a patient via an electrode and the current application unit impresses a signal or a current on the first useful signal path, this current is discharged again via the patient and an appropriately configured return path which is connected to a patient.

An appropriately configured return path for the current on the useful signal path is preferably a low-impedance return path to a common reference potential. Such a return path is, for example, formed by the first interference signal path. Since, due to their high input impedances, the useful signal paths do not form a low-impedance return flow path to the common reference potential (with intact cables), the impressed signal can only be discharged via the interference signal path. The consequence of this is that it is not only the above-described interference signals that are on the interference signal path, but also the signal impressed on the useful signal path.

If a signal measuring cable or a cable of a useful signal path is defective, in addition to the interference signal path, the signal measuring circuit has at least one further low-impedance return path for the impressed current. The impressed signal then passes into the shield and is no longer discharged via the interference signal path since the shield has the lower electrical resistance. Therefore, in the case of a cable defect, the signal on the interference signal path is no longer increased by the signal impressed on the useful signal path, instead, in this case, the impressed signal should be measured on the shield.

This measurement can be performed independently of whether or not the respective cable is connected to the patient. In this way, the cable defect can be identified before or also during an examination and corresponding countermeasures taken, such as, for example, a cable replacement.

In the case of a voltage measuring system as mentioned in the introduction, depending on its application, the signal measuring circuit can have any number of useful signal paths or signal measuring cables. As a rule, a signal measuring circuit, for example an ECG measuring system, has at least two useful signal paths. The useful signal paths preferably comprise electrodes, which can be applied to a patient to be examined in order to measure an electric potential applied there. The electrode structure can depend on the exact type of measurement, for example whether it is an ECG measurement, an EEG measurement or an EMG measurement and on where exactly the potential is to be measured on the patient. Suitable electrodes for different application purposes are known to the person skilled in the art. The output from the electrodes is preferably connected to an amplification circuit, preferably via said signal measuring cables. Particularly preferably, the electrodes are electrically connected to a differential amplifier. This amplifier forms a difference from the signals measured at its inputs and the signals detected by the electrodes and amplifies it. Moreover, the signal measuring circuit has a signal detecting unit, which is connected at the output of the amplification circuit in order to detect the amplified signals or, for example, the potentials and use them further and/or record them. For example, the signal detecting unit can have an A/D converter and further components to further process the digital signal.

The signal measuring circuit of the differential voltage measuring system preferably has a third useful signal path. Furthermore, the signal measuring circuit preferably comprises a driver circuit connected between a current measuring resistor and the signal detecting unit. The driver circuit is also called a “right-leg drive” (RLD) and is responsible for generating a signal, which is regulated to the mean common-mode voltage of individual signals or all the signals. This enables the afore-mentioned measured common-mode interference signals in the useful signal paths to be eliminated.

The third useful signal path (or “right-leg drive path”) provides potential equalization between the patient and the differential voltage measuring system or the ECG measuring system. Herein, the electrode of the third useful signal path is preferably applied to the right leg of the patient, to which the term “right-leg drive” is attributable. However, in principle, this third potential can also be detected at a different point on the patient.

The current application unit preferably in each case impresses different, i.e. unique, signals on different useful signal paths. This is particularly advantageous if the useful signal paths do not all have separate shields, but rather have a common shield, as will be explained in more detail in the following.

As a rule, the shield or other interference signal paths have no direct current components or only very small direct current components. If the signal is impressed on the useful signal path as direct current, this component can be distinguished very easily from alternating current components, which are more frequently coupled-in or otherwise present.

However, otherwise, it can also be advantageous to impress the signal as an alternating current on the useful signal path.

Therefore, the current application unit or current application control unit is preferably embodied to be able to impress an alternating current and/or a direct current on the useful signal paths.

Preferably, the current application unit is embodied such that the signals impressed on the useful signal paths comprise positive currents. Herein, in each case a positive current is impressed on the useful signal paths of the signal measuring circuit.

Therefore, a number of N useful signal paths results in a total signal $I_g$ or total current $I_g$ of:

$$I_g = I_1 + I_2 + \ldots + I_N$$

Therefore, if there is no signal path defect, additionally to any interference signals applied, the total current impressed by the current application units is also discharged via the first interference signal path.

If the signal measuring circuit has a plurality of useful signals, saturation effects may occur if all useful signal paths are exposed to a positive current.

In order to impress different currents or signals on the useful signal paths, the detection apparatus quite particularly preferably has one current application unit per useful signal path. A current application unit preferably comprises a current source. However, particularly preferably, and, as already mentioned, the current application unit comprises a pull-up or pull-down resistor, which regulates the voltages up or down along the useful signal paths and hence indirectly influences the impressed currents on the respective useful signal path.

Herein, the current application unit is preferably embodied to impress a positive current on a number of useful signal paths and a negative current on a number of useful signal paths. Particularly preferably, the number of useful signal paths on which a positive current is impressed matches the number of useful signal paths on which a negative current is impressed. As a result, a useful signal path can be exposed to a positive current and a useful signal path with a negative current in alternation. In the case of one or more cable defects, this results in a total current of:

$$I_D = \sum_i I_{Pi} + \sum_j I_{Nj}$$

$I_D$: defective current $I_{Pi}$: positive current in the defective useful signal path i $I_{Nj}$: negative current in the defective useful signal path j Particularly preferably, the sum total of all defective currents, i.e. all possible combinations of impressed currents, are also unique or individual. If a current can now be measured on the shield, the useful signal path or paths with a signal path defect can be identified quickly and easily from the value of the signal component or components.

It is precisely with complex cable trees with up to 200 leads, as is the case for example with intracardial ECGs as used for example in angiography applications, that this enables targeted detection of the defective lead.

Thus, instead of replacing a complete highly complex cable costing €1000, it is possible to replace a single lead costing €10-20.

In order to check whether the impressed signals on the individual useful signal paths are within the measuring range, the fault detection unit preferably does not comprise one overall comparison unit for all useful signal paths, but instead has one comparison unit for each useful signal path.

Preferably, the comparison units each have an AD converter, however, particularly preferably they also each comprise a comparator.

Due to possible further tolerances and parasitic currents in the voltage measuring system, the impressed signals preferably differ for each useful signal path by at least 5 nA and/or at most 20 nA. Quite particularly preferably by about 10 nA.

In the case of a signal path defect, in order easily to find the useful signal path with the defect, the current application unit is alternatively or additionally preferably embodied to be able to switch the impressed signals individually for each useful signal path. For example, following the detection of a signal path defect, the impression of a signal on a useful signal path can be deactivated gradually in each case. If deactivation of a signal on a useful signal path does not cause a change to the total signal on the interference signal path, this useful signal path has a cable defect.

Preferably, the detection apparatus furthermore comprises at least one first interference signal path for measuring a first interference signal. As described above, common-mode interference signals frequently occur during the measurement of bioelectric signals, for example.

The first interference signal path is preferably connected to the patient via an electrode. Therefore, the third useful signal path can preferably coincide wholly or at least partially with the first interference signal path, as will be explained in more detail below, or correspond thereto at least in sections. For example, the same electrode and the same cable can be used for the third useful signal path and the first interference signal path. Therefore, it is not then necessary for the operator to attach further electrodes to the patient to check the signal path according to at least one embodiment of the invention or to carry out other special measures.

The first and/or the third interference signal path preferably has a current measuring unit. This current measuring unit preferably comprises a current measuring resistor, which is preferably a shunt resistor, and a voltage measuring facility connected in parallel thereto.

Herein, the current measuring resistor can be connected between the third electrode and the driver circuit of the signal measuring circuit, i.e. the right-leg drive.

It preferable for the shunt resistor to have at least one resistance value 10 kΩ and a maximum resistance value of 1000 kΩ.

The voltage measuring facility is preferably also a differential amplifier. At the output of the voltage measuring facility, the interference signal path has an interference signal detecting unit to enable the measured interference signal to be further processed. The interference signal detecting unit comprises, for example, an A/D converter and a unit for further processing the digital signal.

For example, it is possible to search within the first interference signal or a signal resulting or further processed therefrom, for example in the time and/or frequency domain, for typical features of the bioelectric signal, for example, in an ECG signal, for the typical ECG waves.

A detection apparatus according to at least one embodiment of the invention preferably comprises at least one first comparison unit, which checks whether the signal of a useful signal path is within a measuring range.

Preferably a defined measuring range or a threshold value can be selected for this purpose above which it is assumed that the signal flows on the useful signal path.

As a rule, i.e. with intact useful signal paths or cables, the input impedances of the measuring leads of the cables of an ECG measuring systems are high.

If the electrodes are attached to the patient, preferably a check is performed via at least the first comparison unit as to whether the signal which was impressed on the first useful signal path is within a measuring range. At the same time or even after this, at least one first interference signal is measured on at least the first interference signal path.

If, contrary to expectations, the useful signal path is not connected to the patient, for example because the electrode has become detached from the patient, the current circuit is not closed or the impedance to be overcome by the impressed signal is significantly higher.

Therefore, the voltage which was produced by the current application unit, for example at the electrode of the first useful signal path, goes into saturation. Herein, the current can, for example, be detected indirectly via a resistance as a voltage. Hence, the impressed signal lies outside the defined measuring range.

This check or measurement is performed via the comparison unit. Therefore, the comparison unit can check whether or not the useful signal path is connected to a patient. However, on its own this does not provide any information on whether there is a signal path defect of a useful signal path connected to a patient.

Therefore, the impressed current is discharged via the first interference signal path in the case of intact and attached cables but via the shield in the case of a cable defect. Therefore, if it has been established, as described above, that the cables are correctly attached to the patient, a cable defect can be established not only from the current additionally flowing on the shield. The cable defect can also be established from the absence of any current or signal on the first interference signal path. Therefore, two methods for the identification of cable defects can be provided and optionally combined without any significant extra effort.

The detection apparatus preferably has a second interference signal path for measuring a second interference signal. This interference signal path can be constructed in a different way. It can be constructed to ensure that no bioelectric signals are coupled in. However, preferably interference signals can be coupled in that also occur on the first interference signal path, such as, for example, the above-described common-mode interference signals. The second interference signal path can preferably be used for reference measurements for the interference signal on the first interference signal path.

Herein, the second interference signal path does not have to comprise a signal measuring cable but can correspond to a capacitive measurement or coupling to ground.

The second interference signal path preferably extends between a reference potential of the voltage measuring system or the ECG measuring systems and an external reference potential, for example the ground potential. This electrical coupling preferably extends via a capacitive coupling. Since the second interference signal path is only coupled to the voltage measuring system via the common reference potential, the second interference signal on the second interference signal path is largely independent of the input impedances of the cables used in the useful signal paths. Therefore, the second interference signal path cannot be used as a return path for the signals impressed on useful signal paths. Moreover, due to the structure of the second interference signal path, the interference signal is therefore largely determined from common-mode interference signals.

To implement the capacitive coupling, the second interference signal path preferably has a conductor surface electrically connected to the reference potential of the voltage measuring system between the voltage measuring system and the ground potential. Herein, the conductor surface corresponds to a coupling capacitance. The conductor surface can, for example, be implemented by a metal plate or foil.

The second interference signal path can also have a current measuring unit. Herein, the current measuring unit can preferably be connected between the reference potential of the voltage measuring system and the capacitive connection to the external reference potential of the conductor surface. Furthermore, this current measuring unit can also preferably comprise a current measuring resistor and a voltage measuring facility connected in parallel. The current measuring resistor is preferably a shunt resistor and the voltage measuring facility is preferably a differential amplifier.

The second interference signal path can have an interference signal detecting unit, for example at the output of the voltage measuring facility.

The detection apparatus preferably has an interference signal evaluation unit as an analysis unit, which measures a third interference signal at the shield. Hence, the shield serves as a third interference signal path. As described above, this is particularly advantageous since the shield represents an electrical conductor with the same length as the useful signal paths. Ambient electromagnetic fields, which are generally dominated by the common-mode component of the mains frequency, are therefore coupled into the shield similarly into in the useful signal path. This enables a particularly suitable and simplified analysis of the interference signals, in particular in relation to the bioelectric signals to be actually measured.

If at least two interference signal paths are used, the interference signal evaluation unit can preferably be connected to all the interference signal paths. The interference signal evaluation unit is then preferably embodied to form a combination signal of the first interference signal, the second interference signal and/or the third interference signal.

For example, a signal path defect or cable defect can in particular be identified when the signals impressed on the useful signal paths can be detected in the difference signal with the shield or the third interference signal path. Therefore, the difference signal is, for example, composed of the first and/or second interference signal and the third interference signal by way of weighted addition or subtraction. Herein, the weighting can be adapted in a suitable manner.

If a current is impressed on a useful signal path as an alternating current, it may be the case that this current is very similar to the current on the first interference signal path. If a difference signal is now formed from the first and second interference signal, it is easier to detect the currents cross-coupled by the useful signal path.

However, the combination signal can, for example, also comprise a ratio of the first and second interference signal.

The interference signal evaluation unit preferably comprises an interference signal suppressing unit, which is embodied to reduce interference signal components of the useful signals based on at least one of the interference signals determined. This can, for example, take place in that the measured useful signals are reworked as will described in more detail later. However, alternatively or additionally, active counter-regulation via a corresponding driver (RLD) can be performed on the patient even during the detection of the measuring signals.

The range of the mains frequency for the determination of the interference signal is preferably ±2%, particularly preferably ±1%, of a desired mains frequency. This substantially defines the frame that should not be left in the case of a functioning power network. Therefore, it is advantageous to restrict the analysis to this range.

Herein, the actual mains frequency can deviate from the desired value of the desired mains frequency. The desired mains frequency is, for example, 60 Hz in North America, Central America and parts of South America and in Japan, Taiwan, the Philippines etc. or for example 50 Hz in the other parts of the world.

The interference signal suppression preferably takes place in that, for example, the information on this signal is used to set a frequency-based filter, which can advantageously have a narrower bandwidth than was formerly usual in the prior art. The influence of the interference signals and the filter process on the useful signals or the bioelectric signals can advantageously be reduced.

Alternatively, to suppress the interference signals, it is preferably also possible to use a phase-locked loop (PLL) that receives the interference signal determined according to the invention as a generator input signal. A PLL is an electronic circuit arrangement that influences the phase angle and hence also the frequency of a variable oscillator via a closed control loop such that the phase difference between an external reference signal (the interference signal) and a signal derived therefrom is as constant as possible. Hence, the PLL is advantageously provided with very exact information on the frequency of the interference signal so that it now only has to determine the possibly displaced phase or different amplitude of the interference in the useful signals or the bioelectric signals. As a result, the PLL advantageously converges more quickly to the final quality of the interference-suppressed signal.

The detection apparatus according to the invention preferably has an output unit, which is attached to the output of the interference signal evaluation unit and/or operates externally, for example via radio transmission. The output unit is used to output a detected signal path defect or signal immediately. Herein, this outputting or signaling can take place in situ, for example optically or acoustically. Moreover, the signaling can be sent via radio to a service technician for example. A further output form can be performed as logging, for example together with the measurement data. Particularly preferably, the logging is temporally correlated with the measuring signal or the bioelectric signals to be measured. Therefore, it is, for example, possible in the case of interference that occurs intermittently as in the case of a loose connection, to document which measured values can be used and which cannot be used.

In particular, if the detection apparatus is integrated in the voltage measuring system, the output unit is preferably included in a user interface of the voltage measuring system. This, for example, enables the operator simultaneously to check the bioelectric signals on the user interface, for example a monitor, and detect a cable defect.

In the figures, in each case an ECG measuring system 1 is assumed by way of example to be a differential voltage measuring system 1 in order to measure bioelectric signals BS, here ECG signals BS. However, the invention is not limited thereto.

Figure 5:
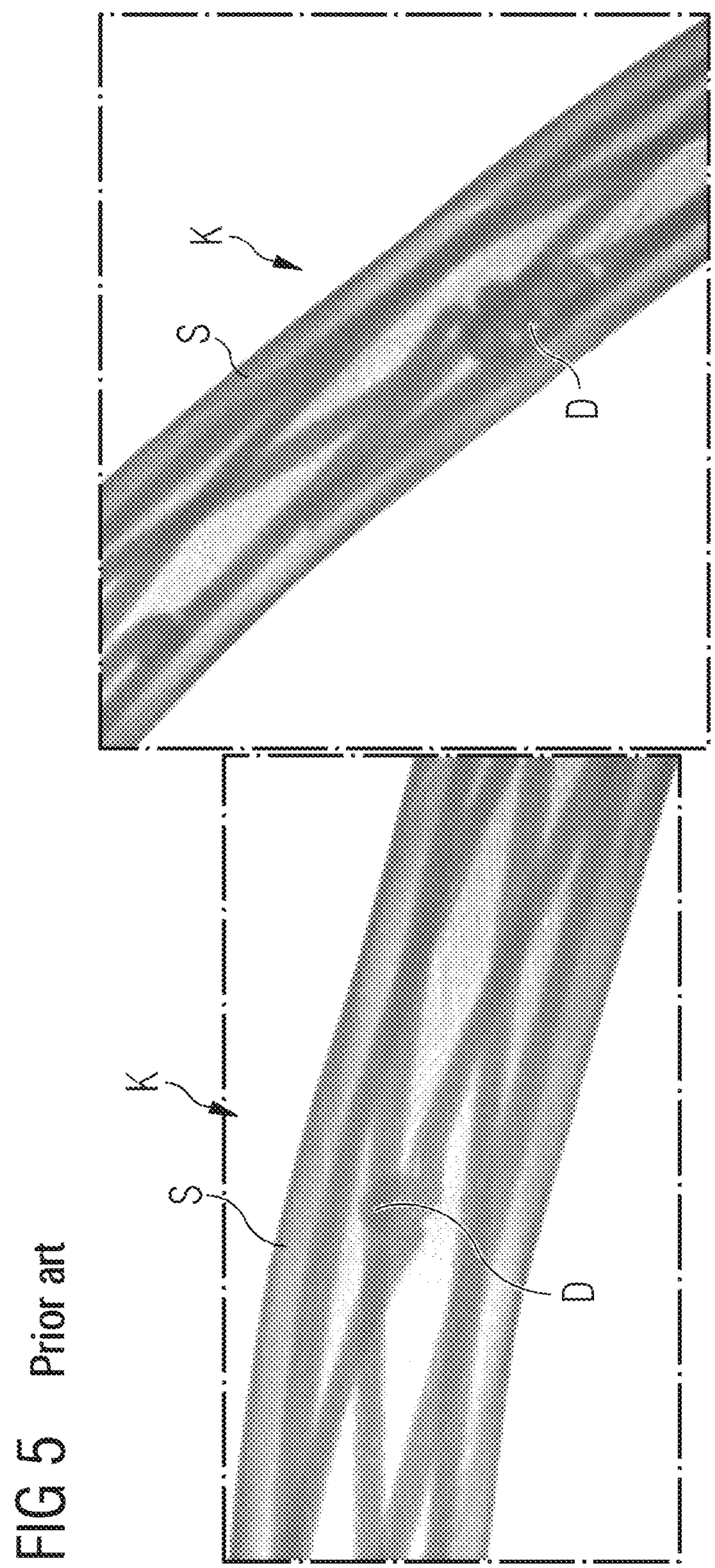

FIG. 1 shows by way of example an ECG measuring system 1 according to the invention, namely a schematic representation of an ECG device 27 with its electrical connectors and electrodes 3, 4, 5 attached thereto by cables K in order to measure ECG signals BS* on a patient P. With the aid of the invention, this ECG measuring system 1 is able to detect a cable defect D (as can be seen, for example, in FIG. 5) in one of the cables K.

To measure the ECG signals BS*, at least one first electrode 3 and a second electrode 4 are required, which are attached to the patient P. Signal measuring cables K connect the electrodes 3, 4 via connectors 25*a*, 25*b*, generally plug-in connectors 25*a*, 25*b*, to the ECG device 27. Herein, the first electrode 3 and the second electrode 4 together with the signal measuring cable K form a part of a signal detecting unit 9 (see FIG. 2) with which the ECG signals BS* can be detected.

A third electrode 5 serves as a reference electrode to create a potential equalization between the patient P and the ECG device 27. This will be explained in more detail later. This third electrode 5 is conventionally attached to the right leg of the patient (for which reason, as explained above, the connector is often also called a "right-leg drive" or "RLD"). However, as in this case, it can be positioned at a different location. Furthermore, via further connectors, which are not shown in the figures, on the ECG device 27 a plurality of further contacts for further leads (potential measurements) can be attached to the patient P and used to form suitable signals.

The voltage potentials UECG34, UECG45 and UECG35, form between the individual electrodes 3,4,5 and these are used to measure the ECG signals BS.

The directly measured ECG signals BS* and/or further-processed bioelectric signals BS are displayed on a user interface 14 of the ECG device 27.

During the ECG measurement, the patient P is at least capacitively coupled to the ground potential E (in FIG. 1, depicted schematically by a coupling on the head and the right leg). However, the patient is exposed to a source of interference Ucm, for example an electrical field produced by the power supply with a 50 Hz alternating current and the resulting interference signal $n_{source}$ (t) via the patient P which constantly changes with time t and which is inevitably also detected by the relatively sensitive measurement. As a rule, this source of interference $U_{cm}$ causes interference signals via the patient P to be coupled into the measuring leads in the signal measuring cables K; this will be referred to later.

Herein, the signal measuring cables K, which lead from the first electrode 3 and the second electrode 4 to the ECG device 27, are part of the useful signal paths 6*a*, 6*b*. Herein, the signal measuring cable K, which leads from the electrode 5 to the ECG device 27, corresponds to part of a third useful signal path 7N. The third useful signal path 7N transfers interference signals from the source of interference Ucm which were coupled in via the patient P and the electrodes.

The cables K have a shield S, which is depicted schematically as a dashed cylinder surrounding all the useful signal paths 6*a*, 6*b*, 7S. However, the shield does not have to surround all the cables K jointly—the cables K can also be shielded separately. However, the connections 25*a*, 25*b*, 25*c* preferably in each case have an integrated pole for the shield. These poles are then brought together on a common shield connector 25*d*. Herein, the shield S is, for example, embodied as a metal foil surrounding the conductor of the respective cable K but insulated from the conductor.

To detect cable defects D, the ECG measuring system 1 according to the invention has a detection apparatus 40, which will be explained in more detail with reference to FIG. 2.

The cables K are checked for cable defects D with the aid of this detection apparatus 40.

The check signal PS generated by the detection apparatus 40, which signals a cable defect D, can, as shown in FIG. 1, be displayed and depicted on an output unit 16' on the user interface 14 of the ECG device 27. As a result, not only the ECG signals BS, but also simultaneously the cables K, can be monitored for a possible cable defect D on the user interface 14.

However, the output unit 16 does not have to be integrated in the user interface 14. The signaling can, for example, also be implemented by a signal lamp, for example in the form of an LED (light-emitting diode) or the like, which signals a defect. However, additionally or alternatively, this can also take place acoustically, for example via a warning bleep. A further variant is an external transfer, for example by radio, to a service technician or to be output in a measuring log in order in this way to display or log a cable defect D. Moreover, as shown in FIG. 1, the ECG device 27 can have an external interface 15 in order, for example, to provide a connector for a printer, a storage facility and/or even a network.

Figure 2:
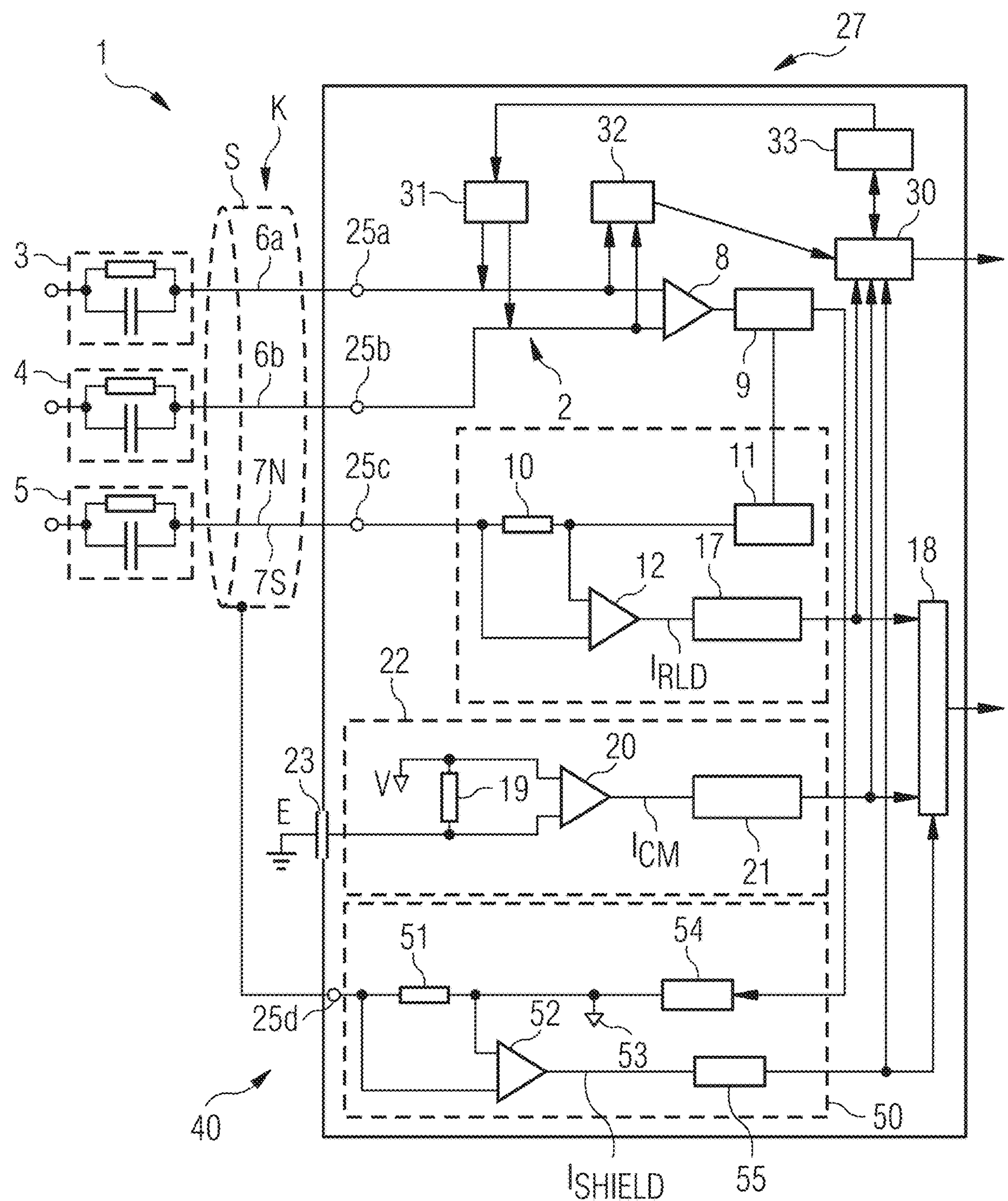

FIG. 2 is an extremely schematic illustration of an example embodiment of the ECG device 27 of the ECG measuring systems 1 in FIG. 1 in more detail in a block diagram.

The ECG measuring system 1 comprises a signal measuring circuit 2, which is used to measure the bioelectric signals BS.

As mentioned above, here the signal measuring circuit 2 has three useful signal paths 6*a*, 6*b*, 7N. The useful signal paths are, as described in respect of FIG. 1, electrically connected via the electrodes 3, 4, 5, the cables K and the plug-in connector 25*a*, 25*b*, 25*c* from the patient P to the ECG device 27. Here, the electrodes 3, 4, 5 are shown simplified as an RC element and illustrate the impedance values of the useful signal paths 6*a*, 6*b*, 7N.

The first electrode 3 and the second electrode 4 are in contact with the patient P. Due to a difference in potential between the lead points at which the electrodes 3, 4 are fastened to the patient, a useful signal, for example a "cardiac current" is transmitted from the electrodes 3, 4 to an amplification circuit 8, for example an operational amplifier. The amplification circuit 8 comprises two inputs and is electrically connected via these with the first electrode 3 and second electrode 4. The output signal of the amplification circuit 8 is transmitted to a signal detecting unit 9, which detects the useful signal amplified by the amplification circuit 8. Herein, the first useful signal path 6*a* extends from the contact of the first electrode 3 to the patient P via the first electrode 3 to the input of the amplification circuit 8. The second useful signal path 6*b* extends from the contact of the second electrode 4 to the patient P via the second electrode 4 to the input of the amplification circuit 8.

The third electrode 5 described in conjunction with FIG. 1 is part of the first interference signal path 7S. It is electrically connected via the cable K to a current measuring resistor 10, hereinafter called a shunt resistor. The shunt resistor 10 is moreover electrically connected to a driver circuit 11, which, as already explained, is also called a right-leg drive. The driver circuit 11 is constructed such that a reference potential which matches the common-mode voltages with ECG components is applied to the patient via the electrode 5. For example, this reference potential can be set in a known manner to an inverse amplified mean value of the measuring leads.

This enables the reference potential to be established at the common-mode voltage.

The detection apparatus 40 moreover comprises a current application unit 31. On the one hand, this can impress a first signal, here a first current IE1 in the nanoampere range, on the first useful signal path 6*a*. On the other hand, it can impress a second signal $I_{E2}$, here a second current $I_{E2}$ in the nanoampere range, on the second useful signal path 6*b*. Moreover, here, the second current $I_{E2}$ is a current that is 10 nA higher than the first current $I_{E1}$.

Currents are regulated via a current application control unit 33, which communicates with the current application unit 31 and a defect analysis unit 30, which will be described later.

In the case of intact signal measuring cables, apart from the interference signal path 7S, there is no further low-impedance return path to the common ground potential for the first current $I_{E1}$ and the second current $I_{E2}$.

This means that it is not only the interference signals ICM that are present on the interference signal path 7S, but also the current $I_{E1}$ impressed on the first interference signal path 6*a* and the current $I_{E2}$ impressed on the second useful signal path 6*b*.

Therefore, with intact useful signal paths 6*a*, 6*b*, the following interference signal IRLD is obtained on the first interference signal path 7S:

$$I_{RLD}=I_{CM}+I_{E1}+I_{E2}$$

Here, the current application unit 31 has only been depicted once by way of example, but it can, for example, be realized via a first current source, which impresses the first current IE1 on the first useful signal path 6*a* and a second current source, which impresses the second current IE2 on the second useful signal path 6*b*.

The voltages that were generated by the current application unit 31 at the first electrode 3 and the second electrode 4 are regularly at the most in the millivolt range. This is because the impressed currents discharge in the nanoampere range through an impedance, which can be in a range of about 50 kOhm to 2 MOhm. Hence, this impedance is in any case lower than that of the useful signal paths. However, if the first useful signal path 6*a* and/or the second useful signal path 6*b* is not electrically connected to the patient P, the current circuit is not closed or the impedance to be overcome by the impressed current is significantly higher. As a result, the voltage generated by the power sources at the electrode, which is not in contact with the patient P, goes into saturation. To check this, the detection apparatus 40 has a comparison unit 32. Here, for clarity, the comparison unit 32 was only depicted as a block. However, here, there is preferably in each case a comparison unit for the first useful signal path 6*a* and for the second useful signal path 6*b*. Here, the comparison units 32 comprise comparators 32. If the currents determined on the first useful signal path 6*a* and on the second useful signal path 6*b* are within a predefined measuring range, the first electrode 3 and the second electrode 4 are electrically connected to a patient and the comparators 32 report two connected electrodes.

If, for example, only one connected electrode is reported, a user of the ECG device can check the electrodes immediately and re-attach them if necessary.

As described above, the electrodes are attached to the ECG device 27 via signal measuring cables K. To make the application of the ECG measuring systems 1 on the patient P as simple as possible, the cables K should be narrow, light and at the same time shielded. However, this combination of features often results in cable defects D (see FIG. 5). Herein, the two cables K depicted in the X-ray images in each case have a cable defect D in the form of a kink D. This cable defect D can occur after bending or torsion of the cables K. This can result in irreversible bulging of the measuring leads, which ruptures the lead insulation. The rupturing of the lead insulation can result in contact between the measuring leads and the shield S. This contact results in a reduction in the input impedance and the amplification of interference.

The reduction in the input impedance of the cable K in the case of a cable defect D results in a further low-impedance return flow path for the respective impressed current via the shield S. If, for example, there is a cable defect D in the first useful signal path 6*a*, the current IE1 discharges via the shield S and hence no longer increases the current IRLD on the interference signal path 7S. However, the comparator 32 does not detect this incorrectly discharged current and continues to indicate that the electrode 3 is electrically connected to the patient P.

To be able now to detect this cable defect D, the detection apparatus 40 has three interference signal paths 7S, 22, 50.

The useful signal paths 6*a*, 6*b* comprise the first electrode 3 and the second electrode 4, the cables K, the current application unit 31, the comparison unit 32 and the further lead inside the device (with the amplification circuit 8) as far as the signal detecting unit 9 and also have a dual function here. Namely, they belong on the one hand to the signal measuring circuit 2 in order to measure bioelectric signals BS. On the other hand, they belong to the detection apparatus 40 to check whether, or optionally how many, electrodes of the corresponding useful signal paths 6*a*, 6*b* are connected to a patient or are defective.

The signal $I_{RLD}$ output by the interference signal evaluation unit 18 is analyzed in a defect analysis unit 30 together with the data from the comparison unit 32. If the comparison units 32 report that all the electrodes are connected and the interference digitization unit 13 outputs a current IRLD comprising the interference signals $I_{CM}$ plus the first impressed current $I_{E1}$ and the second impressed current $I_{E2}$, the defect analysis unit 30 detects that all the electrodes are connected to the patient P and there is no cable defect D.

In the case of a defect, for example in the useful signal path 6*a*, the current IE1 discharges via the shield S. To measure this defective current, the third interference signal path 50 has a current measuring unit 51, 52.

For the third current measuring unit 51, 52, a third shunt resistor 51 is connected to the internal reference potential 53, which can be the same reference potential as V, and the connector 25*d* of the shield S is used as a current measuring resistor. Moreover, a third voltage measuring facility 52 connected in parallel is used. Herein, the third voltage measuring facility 52 can again be implemented by an amplifier, for example by a PGA. The voltage measuring facility 52 is also connected to a third interference signal detecting unit 55, which is, for example, embodied as an A/D converter and digitizes and optionally further processes the measured signals $I_{SHIELD}$.

Moreover, a cable driver 54 is arranged on the third interference signal path 50, which is connected to the signal detecting unit 9. This enables a reference potential complementary to the common-mode voltages to be applied to the shield S. This enables an approximation of the interference fields in the environment or the mains voltage.

Figure 3:
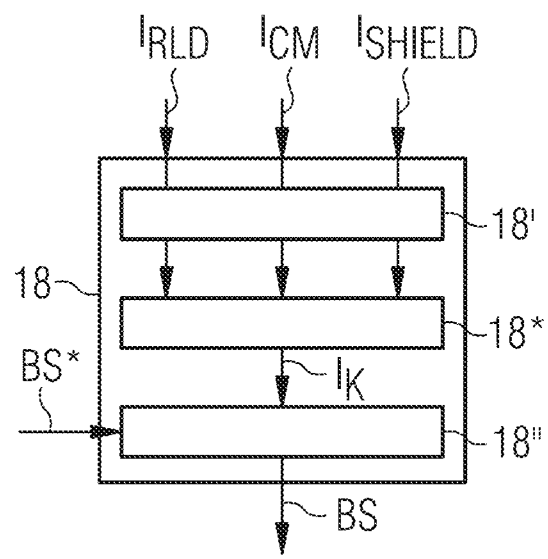
FIG. 3 shows a schematic block diagram of an example embodiment of an interference signal evaluation unit for a detection apparatus according to the invention.

However, the detection apparatus 40 does have to be integrated in the ECG measuring system, as shown, for example, in FIG. 3. It can also be installed in an existing ECG measuring system via plug-in connectors, or even connected upstream or interconnected. Such retrofitting also enables cable defects D to be detected with an existing ECG measuring system.

To display the ECG signals BS* or BS and possible cable defects D via a check signal PS (see FIG. 1) in parallel on the user interface 14, this is attached to the signal detecting unit 9 of the signal measuring circuit 2 and to the defect analysis unit 30 of the detection apparatus 40. This is indicated extremely schematically in FIG. 1. Therefore, the user interface 14 is shown in FIG. 1 with a corresponding output unit 16'.

The above-described further output unit 16 for, for example, optical and/or acoustic signaling of a cable defect D can also be coupled to an output of the interference signal evaluation unit 13 and the defect analysis unit 30.

Moreover, as already mentioned, the differential voltage measuring system 1 is equipped with an external interface 15, for example for a network, a printer and/or a storage device etc., which can, for example, be connected by way of signaling technology to the signal detecting unit 9 of the signal measuring circuit 2 and/or the defect analysis unit 30.

The detection apparatus 40 has three interference signal paths 7S, 22, 50. As with the example embodiment in FIG. 2, the first interference signal path 7S comprises the third electrode 5, which is attached by its input to a patient P and extends as far as the shunt resistor 10, which is electrically connected to the output of the electrode 5. Here, the voltage that drops over the shunt resistor 10 is also measured by the first voltage measuring facility 12 connected in parallel to the shunt resistor 10. The interference signal IRLD measured thereby is then digitized, further processed and detected by a first interference signal detecting unit 17 connected to the output of the first voltage measuring facility 12.

The detection apparatus 40 furthermore comprises a second interference signal path 22 with a current measuring unit 19, 20. This second current measuring unit 19, 20 measures the current flowing from an internal reference potential V of the ECG device 27 via a capacitive coupling to an external fixed reference potential E, the ground potential E. This second measured interference signal ICM is primarily again common-mode interference signals. The capacitive coupling between the ECG device 27 and the ground potential E is still present. In order to provide a defined interference signal path 22 for this interference signal ICM at which the interference signal ICM can be easily measured, a larger conductor surface 23, for example in the form of a metal plate or a foil, is connected to the internal reference potential V of the ECG device 27, which forms a "capacitor surface" to the ground potential E. In this second interference signal path 22, the second current measuring unit 19, 20 is connected between the internal reference potential V and the conductor surface 23.

For the second current measuring unit 19, 20, a current measuring resistor 19, hereinafter called the second shunt resistor, connected between the internal reference potential V and the conductor surface 23 and a second voltage measuring facility 20 connected parallel thereto is used for current measurement on the second interference signal path 22. Herein, the second voltage measuring facility 20 can again be implemented by an amplifier, for example by a PGA.

The measured second interference signal ICM is detected by an interference signal detecting unit 21 connected to the output of the voltage measuring facility 20, for example digitized and optionally further processed by an A/D converter.

The three interference signal detecting units 17, 21, 55 of the respective interference signal paths 7S, 22, 50 are connected to a—here preferably digitally operating—interference signal evaluation unit 18 and to the defect analysis unit 30.

The interference signal evaluation unit 18 is configured to process the first interference signal $I_{RLD}$, the second interference signal $I_{CM}$ and the third interference signal $I_{SHIELD}$. As a result, the common-mode interference on the third interference signal path 50 can be separated or distinguished from the cross-coupled currents $I_{E1}$, $I_{E2}$ that occur there in the case of defective cables K or measuring leads K. This makes it easier for a cable defect D to be detected. To evaluate the interference signals $I_{RLD}$, $I_{CM}$, $I_{SHIELD}$, which are present in digital form here, the interference signal evaluation unit 18 can again be implemented by a computing facility with suitable software and/or for example by one or more ASIC(s).

The interference signal evaluation unit 18 can preferably be embodied such that an output signal is generated from the two interference signals $I_{RLD}$, $I_{CM}$, as will be explained in more detail with reference to FIG. 3.

Figure 4:
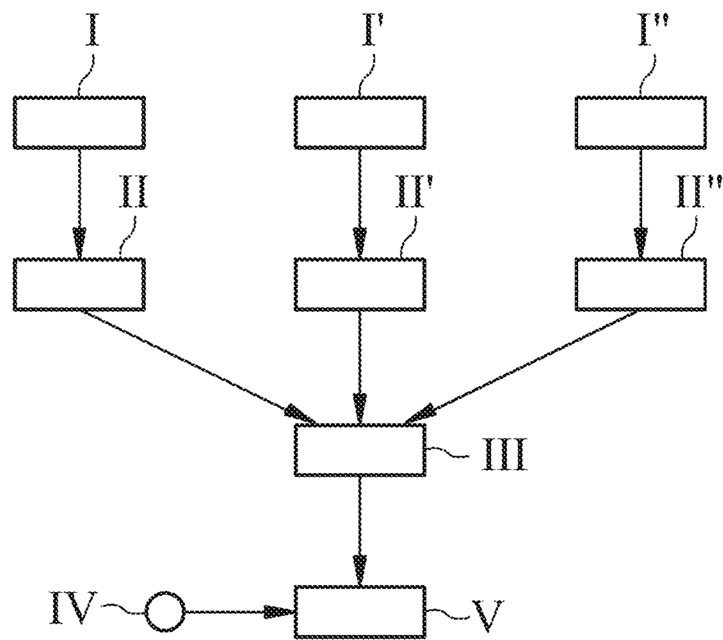
FIG. 4 shows a schematic flow diagram of an example embodiment of a method according to the invention for detecting interference on signal paths in a differential voltage measuring system and FIG. 5 shows X-ray images of two ECG cables with kinks.

FIG. 3 and FIG. 4 are described jointly in the following. Herein, FIG. 3 shows an example embodiment of an interference signal evaluation unit 18 of a detection apparatus according to the invention 40. FIG. 4 depicts an example embodiment of a method according to the invention for detecting interference as a schematic block diagram. In steps I, I', I", the interference signal evaluation unit 18 in each case receives as input signals the interference signals $I_{RLD}$, $I_{CM}$, $I_{SHIELD}$ previously detected in the interference signal detecting units 17, 21, 55.

In an interference signal determining unit 18' of the interference signal evaluation unit 18, interference signals with a frequency in the range of a mains frequency are extracted from the simple measuring signals. This takes place in step II for the first interference signal $I_{RLD}$, in step II' for the second interference signal $I_{CM}$ and in step II" for the third interference signal $I_{SHIELD}$, in each case for example by way of a frequency analysis.

In step III, the signals defined in this way as one frequency are combined in a combination unit 18* of the interference signal evaluation unit 18 to form one combination signal IK. This can, for example, take place by way of weighted addition or subtraction of the signals. Herein, the weighting can be varied as required, i.e., for example, according to the strength of the respective couplings-in or interference fields.

In a step IV, bioelectric measuring signals BS* that were previously determined by the signal measuring circuit are received from the interference signal evaluation unit 18.

The interference signal evaluation unit 18 furthermore comprises an interference signal suppressing unit 18". This is used to reduce the interference signal components based on the interference signal determined. This takes place in step V for example via a narrow-band frequency-based filter, for example with a bandwidth of less than 2 Hz, which is preferably embodied as an adaptive filter, or via a phase-locked loop.

However, alternatively, it is also possible to use a plurality of further algorithms, such as, for example, pattern recognition or a Kalman filter, to evaluate the difference signal $I_k$ or combination signal $I_k$.

Therefore, the detection apparatus according to the invention 40 enables a cable defect D in an ECG-System 1 to be detected immediately and unequivocally. No separate test procedure performed by a trained service technician is required for this. The check on the cables K takes place at the same time as the ECG measurement and defects D can be detected quickly and easily by every operator of the ECG device. Moreover, if different currents are impressed on the useful signal paths, it is also possible to determine which useful signal path has a signal path defect.

If the checked currents which have been impressed on the useful signal paths 6*a*, 6*b* are within the measuring range and, for example, two connected electrodes have been detected and the current measurement on the first interference signal path also measures the currents that were coupled into the first interference signal path via two electrodes, both electrodes are applied and there is no signal path defect. This can also be additionally or alternatively established if none of the impressed currents flows on the shield.

If the checked currents which have been impressed on the useful signal paths 6*a*, 6*b* are within in the measuring range and, for example, two connected electrodes have been detected, but the current measurement on the first interference signal path, for example, only measures one current that was coupled into the interference signal path via an electrode, there is a signal path defect in a useful signal path. However, then the current of the defective useful signal path discharges via the shield and can be alternatively or additionally detected there.

In conclusion, reference is made once again to the fact that the apparatuses and methods described in detail above are only example embodiments which can be modified by the person skilled in the art in wide ranges without departing from the scope of the invention. For example, the differential voltage measuring system does not necessarily have to be an ECG device—it can also be another medical device with which bioelectric signals can be detected, such as, for example, an EEG, EMG etc. Furthermore, the use of the indefinite article "a" or "an" does not preclude the relevant features being present on a multiple basis. Similarly, the term "unit" does not preclude this from comprising a plurality of components, which could also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A detection apparatus to detect interference on signal paths in a differential voltage measuring system, the differential voltage measuring system including a signal measuring circuit configured to measure bioelectric signals, the signal measuring circuit including a number of signal paths, the number of signal paths including at least one shield, and the detection apparatus comprising:

at least one analysis circuit connected to the at least one shield, the at least one analysis circuit configured to detect interference in a signal path among the number of signal paths via a detection signal measured at the at least one shield.

2. The detection apparatus of claim 1, further comprising:

at least one current application circuit configured to impress a first signal on a first signal path among the number of signal paths, and wherein the at least one analysis circuit is configured to detect a signal path defect in the signal path based on measurement of the first signal, the first signal being included in the detection signal.

3. The detection apparatus of claim 2, wherein the at least one current application circuit includes a plurality of current application circuits, each of the plurality of current application circuits being configured to impress a different signal on a different signal path among the number of signal paths.

4. The detection apparatus of claim 3, further comprising:

at least one first comparison circuit configured to check whether a respective signal on a signal path among the number of signal paths is within a measuring range.

5. The detection apparatus of claim 2, further comprising:

a first interference signal path for measuring a first interference signal.

6. The detection apparatus of claim 5, further comprising:

a second interference signal path for measuring a second interference signal.

7. The detection apparatus of claim 6, wherein the at least one analysis circuit is configured to measure a third interference signal at the at least one shield.

8. The detection apparatus of claim 7, wherein the at least one analysis circuit is configured to form a combination signal, the combination signal including at least one of the first interference signal, the second interference signal or the third interference signal.

9. The detection apparatus of claim 7, wherein the at least one analysis circuit is configured to reduce interference signal components of the bioelectric signals based on at least one of the first interference signal, the second interference signal or the third interference signal.

10. The detection apparatus of claim 1, further comprising:

a plurality of current application circuits, each of the plurality of current application circuits being configured to impress a different signal on a different signal path among the number of signal paths.

11. The detection apparatus of claim 1, further comprising:

a first interference signal path for measuring a first interference signal.

12. The detection apparatus of claim 11, further comprising:

at least one first comparison circuit configured to check whether a respective signal on a signal path among the number of signal paths is within a measuring range.

13. The detection apparatus of claim 11, further comprising:

a second interference signal path for measuring a second interference signal.

14. The detection apparatus of claim 13, wherein the at least one analysis circuit is configured to measure a third interference signal at the at least one shield.

15. The detection apparatus of claim 14, wherein the at least one analysis circuit is configured to form a combination signal, the combination signal including at least one of the first interference signal, the second interference signal or the third interference signal.

16. The detection apparatus of claim 11, wherein the at least one analysis circuit is configured to reduce interference signal components of the bioelectric signals based on the first interference signal.

17. The detection apparatus of claim 1, wherein the at least one analysis circuit is configured to:

determine an interference signal with a frequency in a range of a mains frequency; and reduce interference signal components of the bioelectric signals based on the interference signal.

18. The detection apparatus of claim 17, wherein the range of the mains frequency is ±2% of a desired mains frequency.

19. The detection apparatus of claim 17, wherein the range of the mains frequency is ±1% of a desired mains frequency.

20. A voltage measuring system comprising:

at least one signal measuring circuit including a number of signal paths for measuring the bioelectric signals; and the detection apparatus of claim 1.

21. The detection apparatus of claim 1, wherein the detection signal indicates contact between the signal path and the at least one shield.

22. A method for detecting interference on signal paths in a differential voltage measuring system, the differential voltage measuring system including a signal measuring circuit for measuring bioelectric signals, the signal measuring circuit including a number of signal paths, the number of signal paths including at least one shield, the method comprising:

measuring detection signals at the at least one shield; and detecting interference based on analysis of the detection signals.

23. A non-transitory computer program product storing a computer program, the computer program being directly loadable into a storage facility of a voltage measuring system, and the computer program including program segments that, when executed in the voltage measuring system, cause the voltage measuring system to execute the method of claim 22.

24. A non-transitory computer-readable medium storing program segments that, when executed by a computing unit, cause the computing unit to perform the method of claim 22.

* * * * *